United States Patent
Goetsch et al.

(10) Patent No.: US 9,399,739 B2
(45) Date of Patent: *Jul. 26, 2016

(54) PROCESS FOR PRODUCING DISTILLATE FUELS FROM SYNGAS

(71) Applicant: Syngas Technology, LLC, Elk River, MN (US)

(72) Inventors: Duane A Goetsch, Andover, MN (US); Christian T Goralski, Jr., North Oaks, MN (US); Jacqueline R Hitchingham, Anoka, MN (US)

(73) Assignee: SYNGAG TECHNOLOGY LLC, Elk River, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/304,800

(22) Filed: Jun. 13, 2014

(65) Prior Publication Data

US 2015/0361006 A1     Dec. 17, 2015

(51) Int. Cl.
*C10G 2/00* (2006.01)
*C07C 1/04* (2006.01)

(52) U.S. Cl.
CPC .............. *C10G 2/331* (2013.01); *C10G 2/332* (2013.01); *C10G 2/333* (2013.01); *C10G 2/334* (2013.01); *C07C 1/04* (2013.01)

(58) Field of Classification Search
CPC ............ C07C 1/04; C07G 2/32; C10G 2/331; C10G 2/332; C10G 2/333; C10G 2/334
See application file for complete search history.

(56) References Cited

U.S. PATENT DOCUMENTS

| | | | | |
|---|---|---|---|---|
| 6,696,501 B2 * | 2/2004 | Schanke et al. | | 518/705 |
| 2012/0277330 A1 * | 11/2012 | Goetsch et al. | | 518/705 |
| 2013/0065974 A1 * | 3/2013 | Kresnyak | | 518/702 |

* cited by examiner

*Primary Examiner* — Fereydoun G Sajjadi
*Assistant Examiner* — Medhanit Bahta
(74) *Attorney, Agent, or Firm* — Henry E Naylor

(57) ABSTRACT

A process for producing distillate fuels, such as a diesel fuel, from a syngas feedstream having a relatively low $H_2/CO$ ratio of greater than 1 and equal to or less than 2.0. The syngas feedstream is preferably passed to a $CO_2$ removal zone, then to at least one Fischer-Tropsch zone, wherein the resulting Fischer-Tropsch product stream is passed to a separation zone to obtain a hydrocarbon-containing fraction that is hydroconverted to result in a distillate boiling range stream.

15 Claims, 1 Drawing Sheet

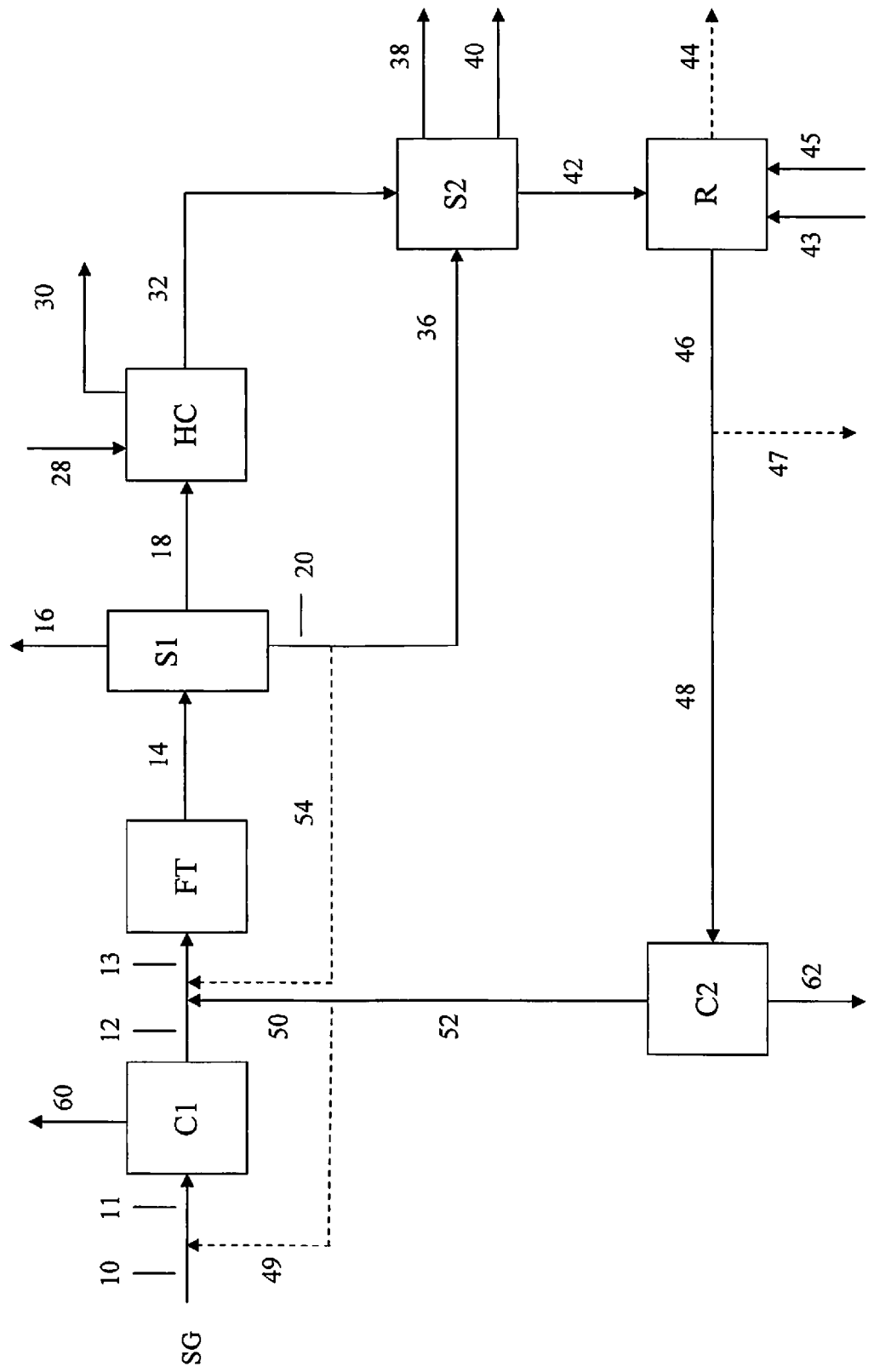

PROCESS FOR PRODUCING DISTILLATE FUELS FROM SYNGAS

CROSS-REFERENCE TO RELATED APPLICATIONS

This application claims benefit of Provisional Application 61/834,847 filed Jun. 13, 2013.

FIELD OF THE INVENTION

This invention relates to a process for producing distillate fuels, such as a diesel fuel, from a syngas feedstream having a relatively low $H_2/CO$ ratio of greater than 1 and equal to or less than 2.0. The syngas feedstream is preferably passed to a $CO_2$ removal zone, then to at least one Fischer-Tropsch zone, wherein the resulting Fischer-Tropsch product stream is passed to a separation zone to obtain a hydrocarbon-containing fraction that is hydroconverted to result in a distillate boiling range stream.

BACKGROUND OF THE INVENTION

There is a significant effort taking place in many parts of the world to produce transportation fuels, particularly gasoline and distillate fuels, from renewable energy sources. For example, research and development in Fischer-Tropsch technology has been on-going for decades to produce diesel fuels from syngas derived from natural gas and coal. More recently, there is a significant effort taking place to convert renewable resources, such as biomass and triglycerides to transportation fuels. Before biomass can be converted to a transportation fuel via the Fischer Tropsch or similar process (synthetic fuel, or synfuel), it must first be converted to a syngas comprised primarily of $H_2$ and CO, which can then be sent to downstream processing to produce various chemical and transportation fuel products. Conversion of biomass to syngas is typically accomplished by gasification that converts the biomass into predominantly carbon monoxide and hydrogen (syngas) by reacting the carbonaceous material of the biomass, at high temperatures, with a controlled amount of oxygen and/or steam. The resulting syngas can be, inter alia, burned directly in internal combustion engines, used to produce methanol and hydrogen, or methanol and dimethyl ether, or converted via the Fischer-Tropsch process into synthetic transportation fuels.

Syngas produced from biomass has a different characteristic composition than syngas produced from coal or natural gas because of differences in the heating value and chemical composition of biomass compared with coal and natural gas. Specifically, syngas produced from biomass has a significantly lower $H_2/CO$ ratio than syngas produced from natural gas because biomass has a lower heating value and is deficient in hydrogen relative to that of natural gas. As such, processes developed to convert high ratio ($H_2/CO>2$) syngas from natural gas are typically inefficient when applied to converting syngas derived from biomass. One way to overcome this problem is to "shift" the ratio of syngas produced from biomass to a higher $H_2/CO_2$ ratio via the water-gas shift reaction. This can result in higher $H_2/CO$ ratio syngas, but can be thermally inefficient because the reaction itself is exothermic and because of the requirement to produce steam, which results in lower thermal efficiency and lower carbon yield to product. There are two well established processes for converting syngas to liquid transportation fuels. One is the Fischer Tropsch process that is used to convert syngas to diesel fuel and typically utilizes syngas having an $H_2/CO$ ratio greater than 2:1. Another is the methanol to gasoline, or MTG process for producing gasoline from syngas via a methanol intermediate. Production of methanol also requires a syngas having a $H_2/CO$ ratio greater than 2. Therefore, a need exists for a an improved process that can efficiently utilize low $H_2/CO$ ratio syngas produced from biomass, or other carbonaceous feedstocks, having a relatively low heating value.

SUMMARY OF THE INVENTION

In accordance with the present invention there is provided A process for producing a distillate boiling range transportation fuel stream from a syngas feedstream, which syngas feedstream is comprised of hydrogen and carbon monoxide, up to about 40 mol. % of other moieties including water and carbon dioxide, substantially no sulfur, and has a hydrogen to carbon monoxide ratio of about 1 to 2, which process comprising:

a) conducting said syngas feedstream to a Fischer Tropsch reaction zone wherein it is reacted in the presence of a Fischer-Tropsch catalyst and under Fisher-Tropsch conditions to result in a Fischer-Tropsch product stream;

b) conducting said Fischer-Tropsch product stream to a first separation zone resulting in an aqueous-containing stream, a gaseous stream containing unreacted syngas, and a Fisher-Tropsch hydrocarbon-containing product stream comprised of both light and heavy hydrocarbons;

c) conducting said Fischer-Tropsch hydrocarbon-containing product stream to a hydroconversion zone wherein it is reacted in the presence of hydrogen and a hydroconversion catalyst and under hydroconversion reaction conditions to result in a hydroconversion gaseous stream and a distillate boiling range stream;

d) collecting said distillate boiling range stream;

e) conducting at least a portion of said gaseous stream from step c) above and at least a portion of the stream containing any remaining unreacted syngas from step b) above to a second separation zone resulting in an aqueous-containing stream, a hydrocarbon-containing stream comprised of hydrocarbons having 5 or more carbon atoms, and a tail-gas stream;

f) collecting said hydrocarbon-containing stream comprised of hydrocarbons having 5 or more carbon atoms;

g) conducting said tail-gas stream to a reforming zone wherein it is reformed in the presence of hydrogen and a reforming catalyst at reforming conditions to result in a reformed syngas stream having a hydrogen to carbon monoxide ratio equal to or greater than that of said syngas feedstream;

h) conducting at least a portion of said reformed syngas stream to said Fischer-Tropsch reaction zone; and i) removing carbon dioxide from at least one gaseous stream in said process in a carbon dioxide removal zone.

In a preferred embodiment, at least a portion of the reformed syngas stream is conducted to a carbon dioxide removal zone to prevent build-up of carbon dioxide in the system.

In another preferred embodiment a carbon dioxide-lean stream from a second carbon dioxide removal zone is conducted to the syngas feed stream prior to it being introduced into a first carbon dioxide removal zone.

In another preferred embodiment of the present invention at least a portion of the carbon dioxide-lean stream is introduced into the carbon-dioxide-lean stream being conducted from a first carbon dioxide removal zone to said first Fischer-Tropsch zone.

In a preferred embodiment of the present invention the syngas is derived from the gasification of a biomass.

BRIEF DESCRIPTION OF THE FIGURE

FIG. 1/1 hereof is a simplified process flow diagram of a preferred embodiment of the present invention for converting a syngas to a distillate fuels.

DETAILED DESCRIPTION OF THE INVENTION

The process of the present invention will produce transportation fuels in the distillate boiling range, which will be from about 150° C. to about 300° C. Non-limiting examples of such fuels include jet fuels, diesel fuels, kerosene, and blending components thereof. Syngas streams suitable for use in the present invention are those having a hydrogen to carbon monoxide ratio of greater than 1 but less than or equal to 2.0, preferably from about 1.2 to about 1.9, and more preferably from about 1.5 to about 1.8. The syngas stream will also contain substantially no sulfur component, but can include up to about 40 mol %, preferably up to about 20 mol %, more preferably up to about 10 mol %, even more preferably up to about 7 mol %, and most preferably up to about 5 mol % of other moieties, comprised primarily of carbon dioxide, water, nitrogen, and argon. At least an effective amount of one or more gaseous streams can be purged from the process to maintain these levels. The major portion of these other moieties, up to about 100%, will typically be carbon dioxide and the sum of hydrogen plus carbon monoxide will preferably be greater than 80 mol %.

Syngas streams that can be used in the practice of the present invention can be derived from any source as long as they meet the above hydrogen to carbon monoxide requirement. It is preferred that the syngas stream be derived from a renewable source, preferably from a biomass, and more preferably from a lignocellulosic feedstock. The "lignocellulosic feedstock," can be any type of plant biomass such as, but not limited to, non-woody plant biomass, cultivated crops, such as, but not limited to, grasses, for example, but not limited to, C4 grasses, such as switchgrass, cord grass, rye grass, *miscanthus*, reed canary grass, or a combination thereof, or sugar processing residues such as bagasse, or beet pulp, agricultural residues, for example, soybean stover, corn stover, rice straw, rice hulls, barley straw, corn cobs, wheat straw, canola straw, rice straw, oat straw, oat hulls, corn fiber, recycled wood pulp fiber, sawdust, hardwood, for example aspen wood and sawdust, softwood, or a combination thereof. Further, the lignocellulosic feedstock can include cellulosic waste material such as, but not limited to, newsprint, cardboard, sawdust, and the like. For urban areas, the best potential plant biomass feedstock includes yard waste (e.g., grass clippings, leaves, tree clippings, and brush) and vegetable processing waste.

Lignocellulosic feedstocks can also include a single specie of fiber or alternatively, a mixture of species of fibers that originated from different lignocellulosic feedstocks. Furthermore, the lignocellulosic feedstock can be comprised of fresh lignocellulosic feedstock, partially dried lignocellulosic feedstock, fully dried lignocellulosic feedstock, or a combination thereof. In general, the term "biomass" as used herein includes all of the terms, plant biomass, liqnocellulosic, cellulosic, and hemicellulosic. It is preferred that the biomass used in the practice of the present invention be comprised of at least about 30 wt. % cellulose, based on the total weight of the biomass.

It is also preferred that the biomass be converted to a syngas by gasification, more preferred by the gasification process disclosed in co-pending U.S. patent application Ser. No. 13/371,282 filed on Feb. 10, 2012, which is incorporated herein, in its entirety, by reference. The biomass is preferably dried before feeding it to a gasifier. It is preferred that the biomass, after drying, contain no more than about 20 wt. %, preferably not more that about 15 wt. %, and more preferably no more than about 10 wt. % water, based on the total weight of the biomass after drying. The biomass is subjected to a size reduction step to reduce it to a size suitable for gasification, or for a feed to a torrefaction step. It is preferred that the size reduction step produce a biomass having an average particle size of about 1 micron to about 3 inches, preferably from about 150 microns to about 1.5 inches, and more preferably from about 300 microns to 1.5 inches. The fibrous structure of the biomass makes it very difficult and costly to reduce its particle size. Non-limiting examples of mechanical size reduction equipment include rotary breakers, roll crushers, jet mills, cryogenic mills, hammermills, impactors, tumbling mills, roller mills, shear grinders, and knife mills. Hammermills are preferred for the practice of the present invention.

It is more preferred that the biomass be reduced in size after torrefying it at moderate temperatures in a substantially oxygen-free atmosphere. Torrefaction increases the energy density of cellulosic materials by decomposing the fraction of hemicelluloses that is reactive. Thus, the energy content per unit mass of torrefied product is increased. Much of the energy that is lost during torrefaction is in an off-gas (tor-gas) that contains combustibles, which can be burned to provide some of the heat required by the torrefaction process. A preferred torrefaction process is taught in co-pending U.S. patent application Ser. No. 12/825,887 filed on Jun. 29, 2010 which is also incorporated herein, in its entirety, by reference.

Torrefaction of biomass of the present invention is conducted at temperatures from about 200° C. to about 350° C., preferably from about 220° C. to about 320° C., more preferably from about 250° C. to about 300° F. During torrefaction, the biomass properties are changed, which results in better fuel quality for combustion and gasification applications. Typically, torrefaction is followed by pelletizing to yield a product that is suitable as a fuel substitute for coal. In this case, the torrefied biomass of the present invention need not be pelletized, but is instead reduced to a particle size that will be suitable for use in a fluid-bed gasifier. In the torrefaction process of the present invention, the hemicelluloses and, depending on severity, some of the constituents in the biomass undergo hydrolysis and dehydration reactions. The process primarily removes $CH_3O-$, $HCOO-$, $CH_3COO-$ functional groups from the hemicellulose and lignin. Hydrolysis reactions can also cleave the C—O—C linkages in the polymeric chains that comprise the major constituents in the biomass. The acidic components in the tor-gas and the ash components in the biomass have the potential to catalyze these reactions. The torrefaction process produces a tor-gas and a solid product having higher energy density than the feedstock and a tor-gas. The solid product can result in char during gasification and can contribute to heat balance needed for the gasifier. Particle size reduction can also occur during this process as a result of chemical action rather than mechanical actions as in grinding. Overall, the process uses less electrical power to achieve a desired degree of size reduction than mechanical size reduction without torrefaction.

The gasification process as applied to the conversion of carbonaceous materials involves many individual reactions associated with conversion of carbon, hydrogen, and oxygen into products involving steam, hydrogen, oxides of carbon, soot or tars and hydrocarbons. At elevated temperatures (>530° C.) associated with gasification, the major products are typically steam and syngas comprised of hydrogen, $CO_2$, CO and methane. Chars and soot represent compounds rich in carbon and may contain small amounts (<5%) of hydrogen.

The present invention can be better understood with reference to the FIGURE hereof which is simplified process flow scheme for practicing a preferred embodiment of the present invention. This FIGURE shows two $CO_2$ removal zones C1 and C2 as a more preferred mode of operation, but it will be understood that only one $CO_2$ removal zone can be used either upstream of Fischer-Tropsch reaction zone FT or anywhere else in the process loop. For example, a $CO_2$ removal zone can be employed downstream of second separation zone S2 or downstream of reforming zone R1. A preferred mode of operation is shown in this FIGURE wherein there are two $CO_2$ separation zones, one to remove $CO_2$ from the syngas feedstream upstream of said Fischer-Tropsch reaction zone FT and one downstream of reforming zone R. This FIGURE shows syngas feedstream SG is conducted via line 10 to a first $CO_2$ removal zone C1. The syngas feedstream can optionally be combined with a portion of reformed tail-gas, line 49, to form stream 11.

Syngas leaving the gasifier will typically need to be cooled and cleaned before it is suitable as a feedstream for chemical synthesis. It will typically contain various constituents that can foul downstream equipment, damage compressors, and poison catalysts used in downstream processes. Solids entrained in the syngas are typically fines that were generated during the attrition of solids circulating in a gasifier, ash generated from the biomass, and soot. Syngas derived from biomass generally contains relatively large amounts of $CO_2$ compared to syngas derived from natural gas and coal. This is a consequence of the low heating value of biomass, as well as the process conditions needed to produce a syngas having the desired $H_2$ to CO ratio for downstream processing, such as for the production of higher value liquid products. The overall yield of desired liquid product from syngas can be increased by removing a target amount of $CO_2$, sometimes removing as much $CO_2$ as possible.

Any suitable $CO_2$ removal technology can be used in the practice of the present invention. Non-limiting examples of such technologies include absorption, adsorption, and the use of membrane technology. Non-limiting examples of absorption technologies include chemical absorption, such as the use of MEA or a caustic, and physical absorption such as Selexol and Rectisol processes. In the Selexol process (now licensed by UOP LLC), the Selexol solvent dissolves (absorbs), acid gases from the feed gas at relatively high pressure, usually about 300 to about 2000 psia (2.07 to 13.8 MPa). The rich solvent containing the acid gases is then let down in pressure and/or steam stripped to release and recover the acid gases. The Selexol process is similar to the Rectisol process, which uses refrigerated methanol as the solvent. The Selexol solvent is a mixture of the dimethyl ethers of polyethylene glycol. Both the Selexol Process and the Rectisol process are well known to those having at least ordinary skill in the art so a detailed discussion of these processes is not necessary for an understanding or enablement of the present invention. The Selexol Process is described in more detail in U.S. Pat. No. 4,581,154 which is incorporated herein, in its entirety, by reference.

Non-limiting examples of adsorption technologies include the use of adsorber beds containing an adsorbent such as alumina or a zeolite. Non-limiting examples of membrane technology include gas separation using an agent such as polyphenyleneoxide or polydimethylsiloxane, or gas adsorption using an agent such as polypropylene.

It is preferred to use multi-stage membrane technology for the removal of $CO_2$, such as that taught in U.S. Pat. No. 8,435,326 which is incorporated herein, in its entirety, by reference. Membranes suitable for use in the practice of the present invention are those that are capable of providing a separation factor of $CO_2$ to $H_2$ of at least about 5 to 1, preferably at least about 7 to 1, and more preferably at least about 10 to 1. This separation factor is not based on the permeation of pure gases, $CO_2$ and $H_2$, but on permeation of those gases from the syngas mixture. Measurements of permeation of pure gases through membranes are unreliable as predictors of separation factors that are obtained from gaseous mixtures. Such membranes are preferred because they have a greater affinity for $CO_2$ to adsorb on certain nano-porous media, such as zeolites and silica. This greater affinity facilitates, and even boosts, permeation through such media, while hindering or blocking all other gaseous species. There are several advantages of using such membranes. First, such a membrane system is energy efficient. While reducing the $CO_2$ concentration at least about 5-fold, the retentate process stream will retain about 65 to 70 vol. % $H_2$. Secondly, such a membrane will yield a relatively high concentration (>85%) $CO_2$ in the permeate. Third, such membranes allow for the adjustment of the desired retentate $CO_2$ and $H_2$/CO levels via adjustments by such things as feed flow, pressure and temperature.

While membranes suitable for use in the practice of the present invention can be of both the so-call Type I and Type-II membranes, the Type II membranes will be preferred and they are generally relatively thin supported nano- and micro-porous materials. Such micro-porous membranes will preferably contain a connected network of about 0.6 nm pores in which small molecules can propagate by diffusion. Process conditions will be chosen such that the membrane becomes >50% saturated with $CO_2$ at the high pressure side. This leads to a very high selectivity for $CO_2$ relative to any other gas molecule, particularly $H_2$. Preferred membrane materials include amorphous silica for operation at temperatures less than about 400° C., micro-porous γ-alumina for operations less than about 200° C., and pore-modified zeolite-Y for operations less than about 100° C. A Type I membrane is defined as a membrane whose permeability for various compounds is only determined by the relative diffusivities of those compounds in the pore structure of the membrane. A Type II membrane is defined as a membrane whose permeability for various compounds is also impacted by the interaction of those compounds with specific active sites within the membrane.

In the case where the syngas steam is taken directly from a gasifier, the pressure of the syngas stream exiting the gasifier will be dependent on the particular gasifier employed. For example, some gasifiers are low pressure gasifiers whereas others are medium to high pressure gasifiers. If the syngas stream is at too low a pressure it will be passed through a compression zone to increase its pressure to at least the operating pressure of the membrane used in $CO_2$ separation zone C1. This pressure will be from about 20 psig to about 1000 psig, preferably from about 50 psig to about 700 psig, and most preferably from about 100 to about 400 psig. The use of the $CO_2$ separation steps is to cost effectively remove an effective amount of $CO_2$ from the syngas stream. It may be desirable to leave some $CO_2$ in the syngas stream to act as a diluent. The amount of $CO_2$ left in the syngas stream will be less than about 25 vol. %, preferably less than about 15 vol. %, and more preferably less than about 5 vol. %, based on the total volume of the syngas stream. A second $CO_2$ removal zone can be used depending on the operating conditions of reforming zone R, particularly if too much $CO_2$ starts to be accumulated in the process. To prevent this, it preferred that a $CO_2$ removal zone be used downstream of reforming zone R, although it can also be located anywhere else in the process loop to treat a $CO_2$-containing gaseous stream.

A $CO_2$-rich stream is rejected via line 60. The resulting $CO_2$-lean syngas stream 12 can optionally be combined with a portion of reformed tail gas 50 to form stream 13. The combination of syngas and reformed tail gas streams 10, 49, 50, and 54 form stream 13 which will preferably have a hydrogen to carbon monoxide ratio greater than about 1.6 but less than or equal to 2.2, preferably greater than 1.6 but less than 2.0, more preferably from 1.7 to 1.9, and most preferably 1.8 to 1.9. Stream 13 is then conducted to Fischer-Tropsch reactor FT where it is converted under conventional Fischer-Tropsch conditions and in the presence of a Fischer-Tropsch catalyst to produce a hydrocarbon liquid product steam 14 that is primarily comprised of paraffinic materials, which are ideal for the production of diesel fuels.

Fischer-Tropsch process conditions include temperatures from about 150° C. to about 300° C. Fischer-Tropsch catalysts are well known in the art and typically contain a Group 7 to Group 10, preferably a Group 8 transition metal on a metal oxide support. Groups of elements referred to in this document are those from the so-called common, or standard Table of the Elements containing Groups 1 to 18. The catalysts may also contain a noble metal promoter(s) and/or crystalline molecular sieves. Non-limiting examples of metals of Groups 7 to 10 are those selected from the group consisting of Fe, Ni, Co, Ru and Re, with cobalt being preferred. A preferred Fischer-Tropsch catalyst comprises effective amounts of cobalt and one or more of a metal selected from the group consisting of Re, Ru, Pt, Fe, Ni, Th, Zr, Hf, U, Mg and La on a suitable inorganic support material, preferably one which comprises one or more refractory metal oxides. In general, the amount of cobalt present in the catalyst is between about 1 to about 50 wt. % based on the total weight of the catalyst composition. The catalysts can also contain basic oxide promoters such as $ThO_2$, $La_2O_3$, MgO, $TiO_2$, and $ZrO_2$, noble metals (Pt, Pd, Ru, Rh, Os, Ir), coinage metals (Cu, Ag, Au), and other transition metals such as Fe, Mn, Ni, and Re. Non-limiting examples of support materials suitable for use herein include alumina, silica, magnesia and titania and mixtures thereof. Useful catalysts and their preparation are known and disclosed in U.S. Pat. No. 4,568,663, which is incorporated herein, in its entirety, by reference and which is intended to be illustrative but non-limiting relative to catalyst selection.

Product stream 14 from Fischer-Tropsch reactor FT will be comprised of a gaseous component and a hydrocarbon liquid component having carbon numbers up to about 100 or more. Fisher-Tropsch liquids are typically comprised of predominantly straight chain paraffins having about 5 to about 10 wt. % olefins and less than about 1 wt. % oxygenates, based on the total weight of the Fischer-Tropsch liquids. This gaseous component will typically be comprised of methane, $CO_2$, water, unreacted syngas, and $C_2$ to $C_7$ hydrocarbons. The unreacted syngas in the gaseous stream will have a lower $H_2/CO$ ratio than the syngas fed to the Fischer-Tropsch reactor because the Fischer-Tropsch reaction consumes $H_2$ at a molar ratio of 2 to about 2.2 times that of CO consumption. By convention, we will refer to this lower ratio of unreacted syngas as "partially reacted syngas" to reflect the understanding that this syngas will have a lower $H_2/CO$ ratio than the syngas fed to the reactor. Product stream 14 is sent to first separation zone S1 where one fraction 16 will be comprised of water that will also typically contain small amounts of alcohols. Another fraction 20 will be comprised of partially reacted syngas, while a third fraction 18, will be comprised of both a light hydrocarbon fraction and a heavy hydrocarbon fraction. The light hydrocarbon fraction will typically be comprised predominantly of hydrocarbons in the carbon range of about C5 to about C20. Less than about 5 wt. % of the C5 to C20 fraction will have hydrocarbons in the range of C20+. The heavy hydrocarbon fraction will typically be comprised of hydrocarbons predominantly in the carbon range of about C8 to C20+. This mixed hydrocarbon product stream from Fischer-Tropsch reaction zone FT is sent to a hydroconversion zone HC via line 18. It will be understood that the term "hydrocarbon" as used herein means molecules comprised of only carbon and hydrogen as well as molecules comprised of carbon, hydrogen, and a small amount of one or more heteroatoms, preferably those selected from oxygen and nitrogen.

Stream 20, containing unreacted syngas, is sent to second separation zone S2. It is preferred that stream 20 have a hydrogen to carbon monoxide ratio substantially the same to stream 13 which is introduced into Fischer-Tropsch zone FT. This is accomplished by concurrently operating Fischer-Tropsch reaction zone FT, and tail-gas reforming zone R, under conditions such that partially reacted syngas stream 20 and the reformed and $CO_2$-lean tail-gas stream 52 have substantially the same $H_2/CO$ ratio as syngas feedstream 13, when mixed together.

Light hydrocracking and predominantly hydroisomerization will preferably take place in hydroconversion zone HC. Any suitable predominantly hydroisomerization catalyst can be used for hydroconversion zone HC. One non-limiting type of catalyst that can be used is a conventional hydrotreating catalysts comprised of at least one Group 6 metal and at least one Groups 8 to 10 metal. Preferred metals include Ni, W, Mo, Co and mixtures thereof. These metals, or mixtures of metals, are typically present as oxides or sulfides on refractory metal oxide supports. The mixture of metals may also be present as bulk metal catalysts wherein the amount of metal is about 30 wt. % or greater, based on the total weight of the catalyst. It is within the scope of this invention that the active metal for the hydrotreating catalyst be one or more noble metals selected from Pt and Pd with or without a Group 6 metal. The more preferred catalysts for use in the present invention are fluorided Group 8 metal-on-alumina containing catalyst compositions. The preferred Group 8 metal is platinum and the most preferred alumina containing support is selected from the group consisting of alumina and silica-alumina. It is to be understood that the alumina-containing component may contain minor amounts of other materials, such as, for example, silica, and the alumina herein encompasses alumina-containing materials.

A preferred fluoride Group 8 metal-on-alumina catalyst comprises about 0.1 to about 2 percent, preferably from about 0.3 to about 0.6 percent Group 8 metal and from about 2 percent to about 10 percent fluoride, preferably from about 5 percent to about 8 percent fluoride, based on the total weight of the catalyst composition (dry basis), said fluoride concentration being referred to herein as the bulk fluoride concentration.

A more preferred catalyst of the present invention will have a fluoride concentration less than about 3.0 weight percent, preferably less than about 1.0 weight percent and most preferably less than 0.5 weight percent at its outer surface layer, provided the surface fluoride concentration is less than the bulk fluoride concentration. The outer surface is measured to a depth less than one one hundredth of an inch. The surface fluoride was calculated from the total fluoride analysis and the electron microscope analysis. The remaining fluoride is distributed with the Group 8 metal at a depth below the outer shell into and within the particle interior. Catalysts of the preferred type are described in detail in U.S. Pat. Nos. 4,919,786 and 4,923,841 both of which are incorporated herein in their entirety.

While alumina-containing support materials are preferred, other suitable metal oxide supports include silica and titania. Preferred aluminas are porous aluminas such as gamma or eta alumina. The acidity of metal oxide supports can be controlled by adding promoters and/or dopants, or by controlling the nature of the metal oxide support, e.g., by controlling the amount of silica incorporated into a silica-alumina support. Non-limiting examples of promoters and/or dopants suitable for use herein include halogen (especially fluorine), phosphorus, boron, yttria, rare-earth oxides and magnesia. Promoters, such as halogens, generally increase the acidity of metal oxide supports while mildly basic dopants, such as yttria and magnesia, tend to decrease the acidity of such supports. Fluorine is the most preferred promoter.

Effective hydroconversion conditions that can be used in the practice of the present invention include temperatures from about 250° C. to about 400° C., preferably about 270° C. to about 350° C., pressures of from about 791 to about 20786 kPa (about 100 to about 3000 psig), preferably about 15 kg/cm to about 175 kg/cm$^2$ (about 200 to about 2500 psig), liquid hourly space velocities of from about 0.1 to about 10 hr$^{-1}$, preferably about 0.1 to about 5 hr$^{-1}$ and hydrogen treat gas rates from about 45 to about 1780 m$^3$/m$^3$ (about 250 to about 10000 scf/B), preferably about 89 to about 890 m$^3$/m$^3$ (about 500 to about 5000 scf/B.

The hydroconversion step can be performed in one or more fixed bed reactors, or reaction zones within a single reactor, each of which can comprise one or more catalyst beds of the same, or different, catalyst. Although other types of catalyst beds can be used, fixed beds are preferred. Such other types of catalyst beds suitable for use herein include fluidized beds, ebullating beds, slurry beds, and moving beds. Interstage cooling or heating between reactors or reaction zones, or between catalyst beds in the same reactor or reaction zone, can be employed since the reaction is generally exothermic. A portion of the heat generated during hydrotreating can be recovered. Where this heat recovery option is not available, conventional cooling may be performed through cooling utilities, such as cooling water or air, or through use of a hydrogen quench stream. In this manner, optimum reaction temperatures can be more easily maintained.

Hydroconversion zone HC requires a hydrogen input stream 28. The reaction product from hydroconversion zone HC is fractionated to produce a gaseous stream 32, which is comprised predominantly of light hydrocarbons with the remainder comprised of permanent gases and a distillate boiling range stream 30.

Gaseous stream 32 is conducted to a second separation zone S2. The exiting tail gas stream 42 from separation zone S2 is substantially free of water and hydrocarbons having 5 or more carbon atoms, and is predominantly comprised of CO$_2$, methane and other light hydrocarbon gases, as well as unreacted syngas, with smaller amounts of accumulated atmospheric gases from recycle such as N$_2$ and argon. Water is removed via line 38 and hydrocarbons having 5 or more carbon atoms are collected via line 40 as a naphtha blend stream. The naphtha blend stream composition can be varied to achieve a predetermined boiling point range, but will preferably be comprised predominantly of hydrocarbons in the carbon range of about C5 to about C10.

The resulting tail-gas stream is conducted via line 42 to reforming zone R, where it is reformed to a syngas having a hydrogen to carbon monoxide ratio equal to or greater than that of stream 10 and greater than that of stream 20. Any reforming technology known to one skilled in the art can be used in R, including but not limited to stream reforming, autothermal reforming, as well as partial oxidation. Depending on the input requirements of the chosen reforming process, steam, oxygen, and/or a fuel can be introduced into R via lines 43 and 45.

The process of the present invention will preferably include one or more locations where a fraction of the gaseous stream can be purged in order to prevent accumulation of contaminants such as nitrogen and argon. The optimal location(s) of these one or more purge stream(s) will depend on the specific equipment configuration and can be readily determined by one skilled in the art. Two more preferred embodiments of this purge step are shown in the FIGURE hereof, as a side product from R (stream 44) and as a direct purge from the reformed tail gas stream (stream 47). One skilled in the art will also recognize that the purge stream(s) may contain components that could be either utilized directly or could be recovered using known separation techniques for either use within this process or export. It is preferred to conduct a purge to keep the CO$_2$ level less than about 40

The process of the present invention will also have one or more gas compression steps (not shown) to offset the pressure drop across process equipment. The optimal location(s) of these one or more compression steps will depend on the specific equipment configuration and can be readily determined by one skilled in the art.

The syngas product stream (reformer syngas) from reforming zone R is conducted via lines 46 and 48 to second CO$_2$ removal zone C2, which is an optional CO$_2$— removal zone depending on how the reformer is run. For example, the reformer can be run to achieve a high ratio of H$_2$ to CO. That is, at ratios higher than the ratio of H$_2$ to CO in the syngas feedstream 10, or higher than the ratio of H$_2$ to CO in stream 13 to Fischer-Tropsch zone FT. CO$_2$ is rejected via line 62. The resulting CO$_2$-lean reformed tail gas stream 52 is conducted back to mix with the feeds to one or both of the Fisher-Tropsch reaction zone FT. It will be understood that the resulting CO$_2$-lean tail gas stream 52, depending on the level of CO$_2$, can be split into two equal or unequal fractions 49 and 50. It will also be understood that first CO$_2$ removal zone can be eliminated and CO$_2$ removed from the process after the reformer in second CO$_2$ removal zone C2.

What is claimed is:

1. A process for producing a distillate boiling range transportation fuel stream from a syngas feedstream derived from a biomass, which syngas feedstream is comprised of hydrogen and carbon monoxide, up to about 40 mol. % of other moieties including water and greater than 5 volume percent carbon dioxide, and has a hydrogen to carbon monoxide ratio of greater than 1.5 to 2, which process comprising:
   a) conducting said syngas feedstream to a first carbon dioxide removal zone wherein carbon dioxide is removed to result in a carbon dioxide lean syngas stream having less than 5 volume percent carbon dioxide;
   b) conducting said carbon dioxide lean syngas stream to a Fischer Tropsch reaction zone wherein said carbon dioxide lean syngas stream is reacted in the presence of a Fischer-Tropsch catalyst and under Fisher-Tropsch conditions to result in a Fischer-Tropsch product stream;
   c) conducting said Fischer-Tropsch product stream to a first separation zone resulting in an aqueous-containing stream, a gaseous stream containing unreacted syngas, and a first Fisher-Tropsch product hydrocarbon-containing stream;

d) conducting said Fischer-Tropsch hydrocarbon-containing product stream to a hydroconversion zone wherein said Fischer-Tropsch hydrocarbon-containing product stream is reacted in the presence of hydrogen and a hydroconversion catalyst and under hydroconversion reaction conditions to result in a hydroconversion gaseous stream and a distillate boiling range stream;

e) collecting said distillate boiling range stream;

f) conducting said gaseous stream from step d) above and the stream containing any remaining unreacted syngas from step c above to a second separation zone resulting in an aqueous-containing stream, a hydrocarbon stream comprised of hydrocarbons having 5 or more carbon atoms, and a tail-gas stream;

g) collecting said hydrocarbon stream comprised of hydrocarbons having 5 or more carbon atoms;

h) conducting said tail-gas stream to a reforming zone wherein said tail-gas stream is reformed in the presence of hydrogen and a reforming catalyst at reforming conditions to result in a reformer syngas stream having a hydrogen to carbon monoxide ratio equal to or greater than that of said syngas feedstream having a carbon dioxide level greater than 5 volume percent;

i) conducting at least a portion of said syngas stream from said reforming zone to a second carbon dioxide removal zone wherein carbon dioxide is removed to result in a carbon dioxide lean tail-gas stream having less than 5 volume percent carbon dioxide;

j) conducting at least a portion of said tail-gas stream to said FischerTropsch reaction zone.

2. The process of claim 1 wherein the ratio of hydrogen to carbon monoxide of the syngas feedstream is from about 1.6 to about 1.9.

3. The process of claim 1 wherein at least a fraction of the unreacted syngas stream from said first separation zone is conducted back to said Fischer-Tropsch reaction zone.

4. The process of claim 1 wherein an effective amount of a gaseous stream from at least one process unit in the process is purged from the process to prevent accumulation of contaminants.

5. The process of claim 4 wherein an effective amount of said syngas from said reforming zone is purged.

6. The process of claim 4 wherein an effective amount of gaseous stream is purged downstream of said second separation zone.

7. The process of claim 1 wherein the syngas is received via the gasification of a biomass.

8. The process of claim 1 wherein the biomass is selected from the group consisting of non-woody plant biomass, cultivated crops, grasses, sugar processing residues, agricultural residues, and a combination thereof.

9. A process for producing a distillate boiling range transportation fuel stream from a syngas feedstream obtained from the gasification of a biomass, which syngas feedstream is comprised of hydrogen and greater than 5 volume percent carbon monoxide, up to about 40 mol. % of other moieties including water and carbon dioxide, and has a hydrogen to carbon monoxide ratio of about 1.6 to 1.9, which process comprising:

a) conducting said syngas feedstream to a first carbon dioxide removal zone wherein carbon dioxide is removed to result in a carbon dioxide lean syngas stream having less than 5 volume percent carbon dioxide;

b) conducting said carbon dioxide lean syngas stream to a Fischer Tropsch reaction zone wherein said carbon dioxide lean syngas stream is reacted in the presence of a Fischer-Tropsch catalyst and under Fisher-Tropsch conditions to result in a Fischer-Tropsch product stream;

c) conducting said Fischer-Tropsch product stream to a first separation zone resulting in an aqueous-containing stream, a gaseous stream containing unreacted syngas, and a first Fisher-Tropsch product hydrocarbon-containing stream;

d) conducting said Fischer-Tropsch hydrocarbon-containing product stream to a hydroconversion zone wherein said Fischer-Tropsch hydrocarbon-containing product stream is reacted in the presence of hydrogen and a hydroconversion catalyst and under hydroconversion reaction conditions to result in a hydroconversion gaseous stream and a distillate boiling range stream;

e) collecting said distillate boiling range stream;

f) conducting said gaseous stream from step above and the stream containing any remaining unreacted syngas from step c) above to a second separation zone resulting in an aqueous-containing stream, a hydrocarbon stream comprised of hydrocarbons having 5 or more carbon atoms, and a tail-gas stream;

g) collecting said hydrocarbon stream comprised of hydrocarbons having 5 or more carbon atoms;

h) conducting said tail-gas stream to a reforming zone wherein said tail-gas stream is reformed in the presence of hydrogen and a reforming catalyst at reforming conditions to result in a reformer syngas stream having a hydrogen to carbon monoxide ratio equal to or greater than that of said syngas feedstream having a carbon dioxide level greater than 5 volume percent;

i) conducting at least a portion of said reformer syngas stream to a second carbon dioxide removal zone wherein carbon dioxide is removed to result in a carbon dioxide lean reformer syngas stream having less than 5 volume percent carbon dioxide;

j) conducting at least a portion of said carbon dioxide lean reformer syngas stream to said FischerTropsch reaction zone.

10. The process of claim 9 wherein at least a fraction of the unreacted syngas stream from said first separation zone is conducted back to said Fischer-Tropsch reaction zone.

11. The process of claim 9 wherein an effective amount of a gaseous stream from at least one process unit in the process is purged from the process to prevent accumulation of contaminants.

12. The process of claim 11 wherein an effective amount of said syngas from said reforming zone is purged.

13. The process of claim 11 wherein an effective amount of gaseous stream is purged downstream of said second separation zone.

14. The process of claim 9 wherein the syngas is obtained from a biomass.

15. The process of claim 14 wherein the biomass is selected from the group consisting of non-woody plant biomass, cultivated crops, grasses, sugar processing residues, agricultural residues, and a combination thereof.

* * * * *